(12) United States Patent
Farrell

(10) Patent No.: US 6,935,857 B1
(45) Date of Patent: *Aug. 30, 2005

(54) ORAL APPLIANCE

(76) Inventor: Christopher John Farrell, 1st Floor, Helensvale Plaza, Sir John Overall Drive, Helensvale, QLD 4210 (AU)

( * ) Notice: Subject to any disclaimer, the term of this patent is extended or adjusted under 35 U.S.C. 154(b) by 0 days.

This patent is subject to a terminal disclaimer.

(21) Appl. No.: 10/070,349

(22) PCT Filed: Sep. 29, 1999

(86) PCT No.: PCT/AU99/00840

§ 371 (c)(1),
(2), (4) Date: Aug. 16, 2002

(87) PCT Pub. No.: WO00/35369

PCT Pub. Date: Jun. 22, 2000

(30) Foreign Application Priority Data

| Dec. 16, 1998 | (AU) | ................................. PP7743 |
| Jul. 2, 1999 | (AU) | ................................. PQ1386 |

(51) Int. Cl.$^7$ ............................................. A61C 3/00
(52) U.S. Cl. ........................................ 433/6; 128/861
(58) Field of Search ................... 433/6; 128/853, 128/860, 861, 862

(56) References Cited

U.S. PATENT DOCUMENTS

| 3,211,143 A | * | 10/1965 | Grossberg | .................... 128/862 |
| 5,031,638 A | * | 7/1991 | Castaldi | ....................... 128/861 |
| 5,092,346 A | | 3/1992 | Hays et al. | .................. 128/859 |
| 5,406,963 A | | 4/1995 | Adell | .......................... 128/861 |
| 5,566,684 A | | 10/1996 | Wagner | ...................... 128/861 |
| 5,624,257 A | * | 4/1997 | Farrell | ............................ 433/6 |
| 5,826,581 A | | 10/1998 | Yoshida | ...................... 128/859 |

FOREIGN PATENT DOCUMENTS

| CA | 2024799 AA | 7/1991 |
| EP | 0 801 937 A1 | 10/1997 |
| FR | 2 639 531 A1 | 6/1990 |
| WO | WO 93/08761 | 5/1993 |

* cited by examiner

*Primary Examiner*—John J Wilson
(74) *Attorney, Agent, or Firm*—Caesar, Rivise, Bernstein, Cohen & Pokotilow, Ltd.

(57) ABSTRACT

The oral appliance, either a mouthguard or an orthodontic device, includes a base member having a U-shaped form corresponding to a row of teeth of a user. The base member has inner and outer flanges interconnected by a web which collectively define upper and lower channels within which respectively the upper and lower rows of teeth of the user are received. Upper and lower teeth engaging elements are positioned within the upper and lower channels. The teeth engaging elements are made of EVA which softens at a temperature of 90–95° C. The appliance may also include a tongue tag (25) and breathing apertures (30).

10 Claims, 11 Drawing Sheets

ORAL APPLIANCE

This invention relates to an oral appliance.

More specifically this invention relates to an oral appliance which is capable of being customised to suit the mouth or oral cavity of a patient or user. This invention also relates to a method of making this appliance using moulding techniques.

This invention finds particular but not exclusive application as a mouth guard for use in sports and as an orthodontic appliance for use in correcting myofunctional and tooth alignment problems. It will therefore be convenient to describe the appliance with reference to these example applications. However it is to be clearly understood that the appliance is capable of other applications.

While customised orthodontic appliances are known, these are relatively costly. This is because each appliance has to be made individually and separately in a laboratory after a mould or impression of the patient or user's mouth has been obtained. Naturally it would be advantageous if an appliance could be devised which could be mass produced and which was also capable of being adjusted to fit the dimensions of a particular patient's mouth on the spot while the patient was sitting in a dental chair.

Similarly, while customised sports mouthguards are the guards of choice amongst sports people, they are expensive. While mass produced sports mouthguards are known, they have some real limitations. Specifically, because of a wide range of user mouth sizes and shapes, they often do not fit snugly into the mouth of the user. It would also therefore be advantageous if an appliance could be devised which was mass produced and which was also capable of being customised to fit snugly into a user's mouth.

The applicant has already developed an oral appliance for repositioning the temporomandibular joint. Broadly the appliance comprises a base portion having inner and outer flanges which form respectively upper and lower U-shaped channels for receiving the teeth of upper and lower jaws of a user. The oral appliance is described in detail in the applicant's prior applications PCT/AU90/00399 and PCT/AU92/00592 which are incorporated directly herein by cross reference. The oral appliance correctly positions the temporomandibular joint and positions the lower jaw downwardly and outwardly. This produces advantageous athlete performance as well as a more correct orthodontic positioning of the lower jaw relative to the upper jaw. This encourages an improvement in oral habits and can also provide relief for headaches etc. and other pain conditions.

However, the appliance described above is not capable of being customised to fit a user's mouth. It would therefore be advantageous if a device which had this ability could be innovated.

According to one aspect of this invention there is provided an oral appliance for placing in the mouth of a user, including:

a base member having a generally U-shaped form corresponding to the outline of a jaw of a user, the base member having inner and outer flanges interconnected by a web which define at least one of upper and lower channels within which the corresponding rows of teeth of a user are received; and a continuous layer of thermoplastic material that encompasses the base member thereby to firmly and securely mount the layer of thermoplastic material on the base member, the layer of thermoplastic material forming upper and lower teeth engaging elements which can be conformed or moulded to suit the individual teeth of a user by heating to a temperature at which the layer is plastic and formable.

In one form the base member may define an upper channel within which the upper row of teeth of a user is received. In another form the base member may define a lower channel within which the lower row of teeth of a user are received. In a preferred form the base member defines both upper and lower channels within which respectively the upper and lower rows of teeth of a user are received.

Preferably, the layer of thermoplastic material is formed of EVA (ethylvinylacetate) which softens at a temperature of 90° C.–95° C. The layer of thermoplastic material, e.g. EVA, may have a thickness of 1 mm–4 mm, preferably 1 mm–3 mm, e.g. about 2 mm. EVA has a suitable level of pliability and formability when heated to its softening temperature.

Advantageously, the base member is made of a plastics material which is rigid at temperatures of 90° C.–95° C.

While EVA is preferred for the teeth engaging elements, any thermoplastic having a suitable softening temperature may be used. Preferably the element is malleable at a temperature below 100° C., eg so that it can be softened by immersion in boiling water.

Thus the continuous layer also covers a region of the base member intermediate the upper and lower channels, e.g. the outer walls of the flanges, as well as the channels. The layer encases the base member to firmly and securely mount teeth engaging elements on the base member without delamination. This overcomes the problem of getting EVA to bond to the base member.

In this specification, the term "engaging" shall bear a broad meaning and shall not be interpreted to mean "retaining" or "latching engagement".

Thus the upper and lower teeth engaging elements are capable of being moulded to suit the teeth and jaws of a particular user by being heated above their softening point, eg by being immersed in boiling water and then inserted into the mouth of the user. The formable thermoplastic teeth engaging elements can then be conformed to the dimensions and other characteristics of the teeth and jaw of the user. This provides a customised mouth guard or orthodontic positioning appliance without the need for time consuming moulds to be taken of a patient's mouth.

The temperature to which the elements must be heated must be reasonable bearing in mind that the appliance is to be placed in the mouth of a patient. It is also important that the thermoplastic does not have any other toxic or other undesirable properties.

Preferably the continuous layer of thermoplastic material covers substantially the entire surface area of the base member and the layer is permanently attached to the base member at the time of manufacture. It is to be understood however that this arrangement is not essential and that the layer may be continuous without covering the entire surface area of the base member.

Preferably, the oral appliance forms a single integral article.

It will be understood that other plastics which are sufficiently strong and rigid and which do not have thermoplastic properties in the appropriate temperature ranges may also be used for the base member.

Thus the base member is reasonably rigid while the teeth engaging elements are softer than the base member.

Optionally the base member may have breathing apertures defined therein, eg centrally positioned, for permitting breathing therethrough. In a preferred form, there are four elongate slot-like apertures defined in the base member.

Typically the appliance also includes a tongue tag, eg centrally positioned, defined in the inner flange, for correctly positioning the tongue of a user during use.

In one preferred embodiment, the oral appliance is adapted for use as an orthodontic appliance. In another preferred embodiment, the appliance is suitable for use as a sports mouth guard.

According to another aspect of this invention there is provided a method of making an oral appliance, the method including the steps of:

moulding a base member from plastic material in a first moulding step in a first mould, the member having a generally U-shaped form corresponding to the outline of the jaw of a user and inner and outer flanges interconnected by a web which define at least one of upper and lower channels within which the corresponding rows of a teeth of a user are received;

removing the base member from the first mould and placing it in a second mould having a larger mould cavity and moulding a continuous layer of thermoplastic material onto the base member to form upper and lower teeth engaging elements capable of being customised to suit the mouth of a user, the layer encasing the member to thereby firmly and securely mount the layer of thermoplastic material on the base member.

In one form the base member may define an upper channel within which the upper row of teeth of a user is received. In another form the base member may define a lower channel within which the lower row of teeth of a user is received In a preferred form the base member may define both upper and lower channels within which respectively the upper and lower rows of teeth of a user are received.

Preferably, the base member is injection moulded from polyurethane, polyethylene, polypropylene or santoprine and the layer is injection moulded from EVA.

Thus, the oral appliance may be formed in a two step injection moulding process. More specifically, the base member may be injection moulded in a first die or mould and then when it has been formed it is removed from the first die and locked into a second die or mould where the layer encasing the member is injection moulded. Thus the teeth engaging elements surround or enclose the base member to effect attachment to the base member.

Other features of respectively the base member and teeth engaging elements may be as described above with reference to the first aspect of the invention.

An oral appliance in accordance with this invention may manifest itself in a variety of forms. It will be convenient to hereinafter describe in detail two preferred embodiments of the invention with reference to the accompanying drawings. However it is to be clearly understood that the specific nature of this description does not supersede the generality of the preceding broad description of the invention. In the drawings.

Figure 1:
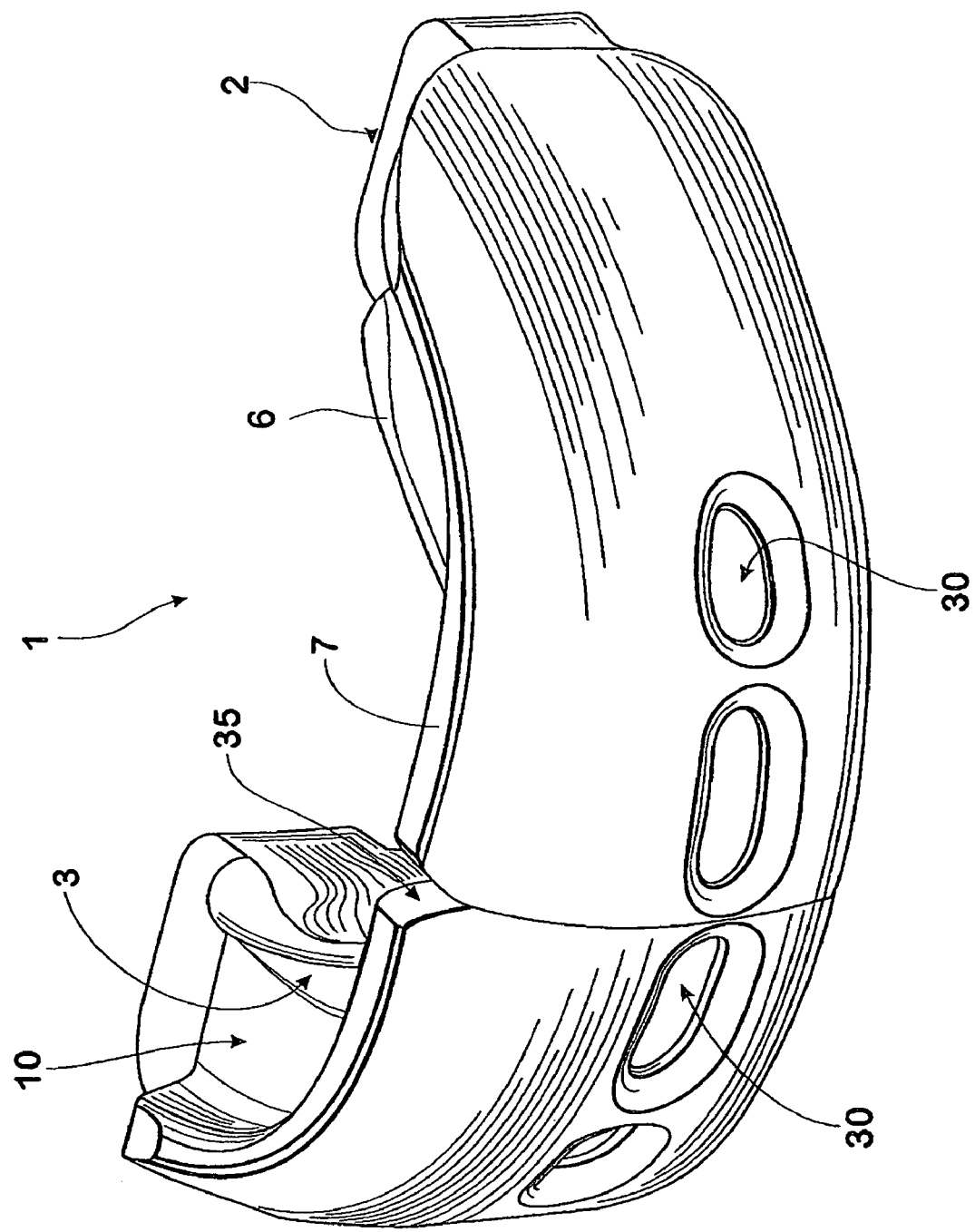
FIG. 1 is a front three dimensional view of an oral appliance in accordance with one embodiment of the invention.
Figure 2:
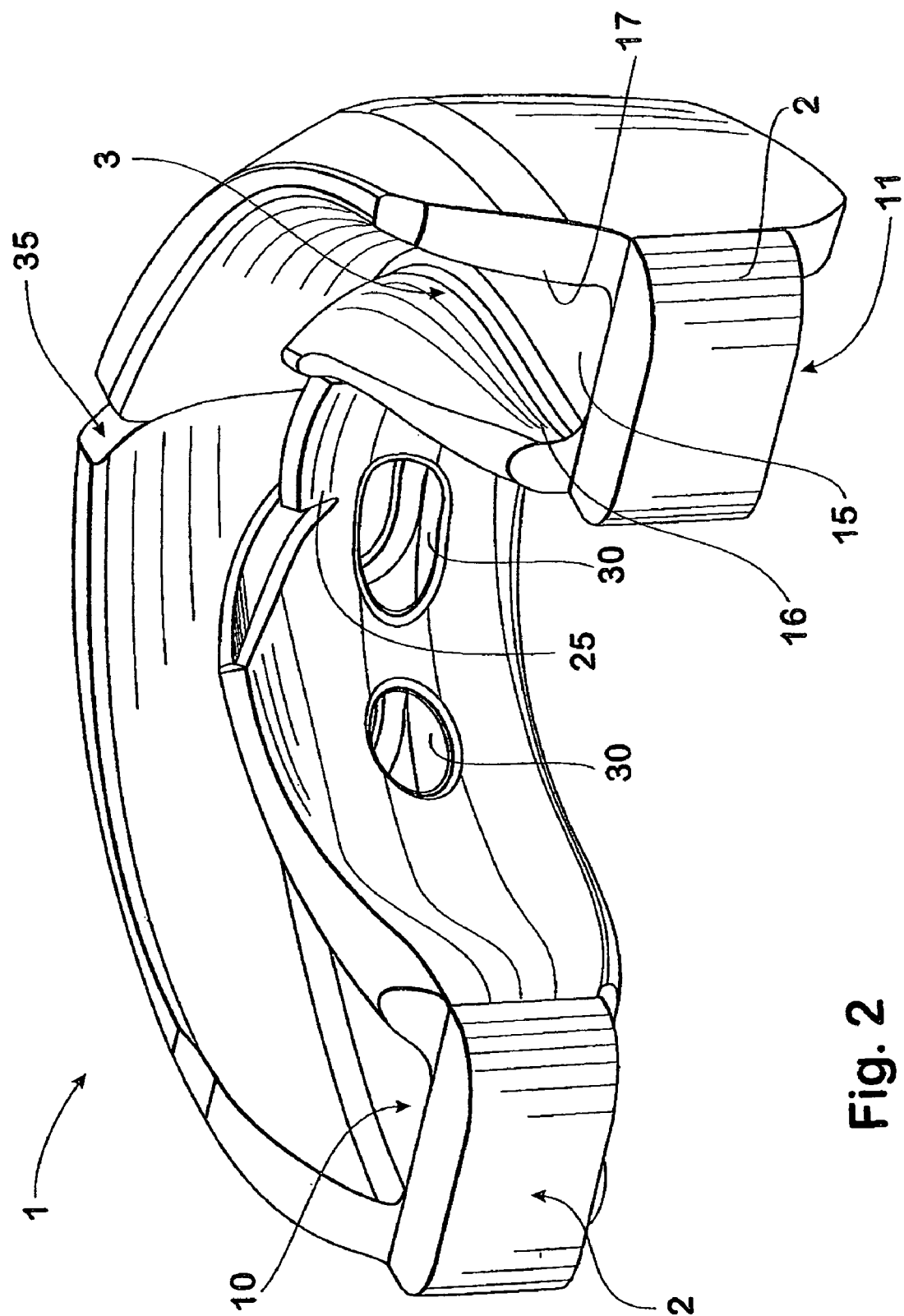
FIG. 2 is a rear three dimensional view of the oral appliance of FIG. 1.
Figure 3:
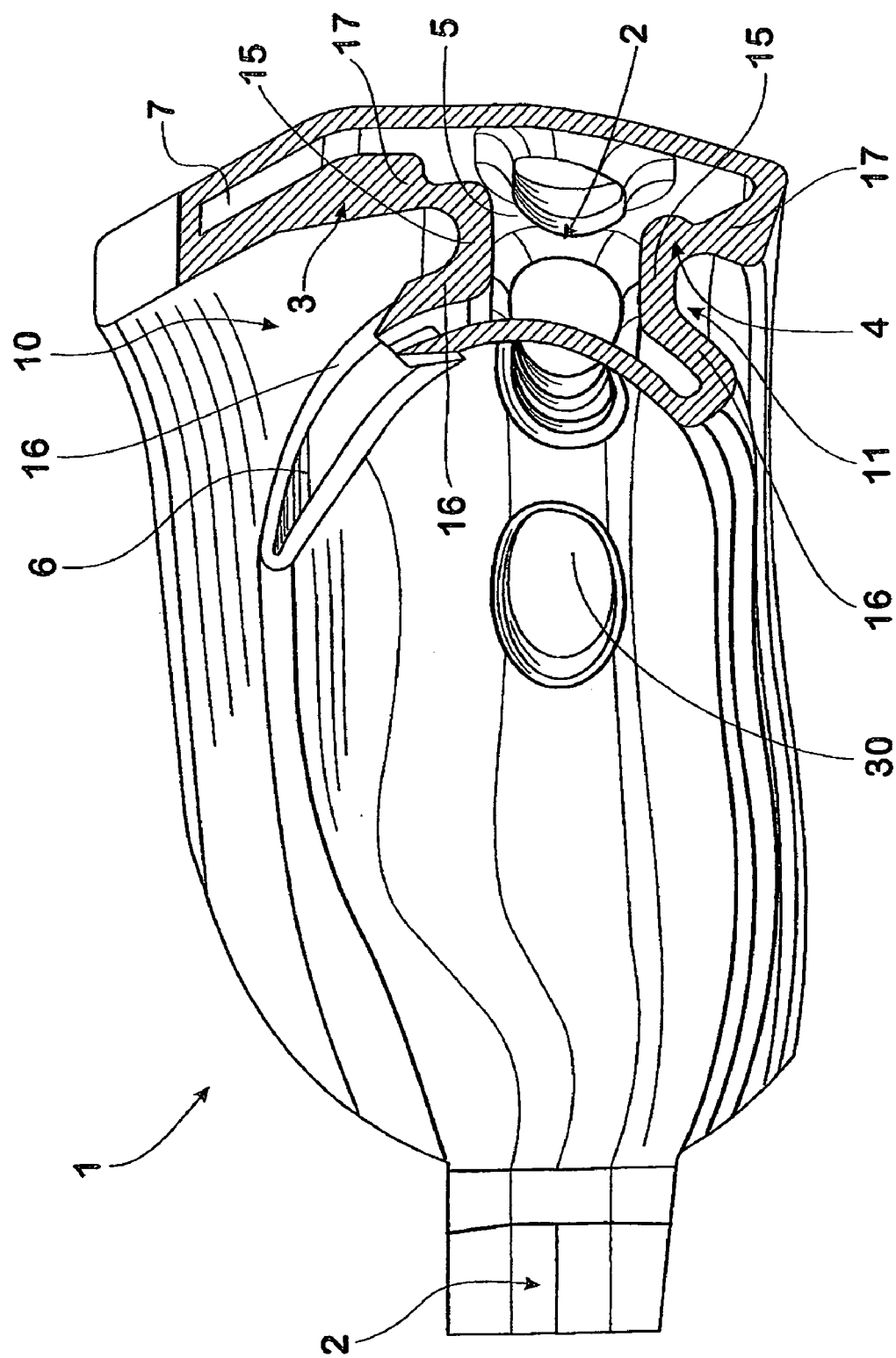
FIG. 3 is a part sectional side view of the appliance of FIG. 1.
Figure 4:
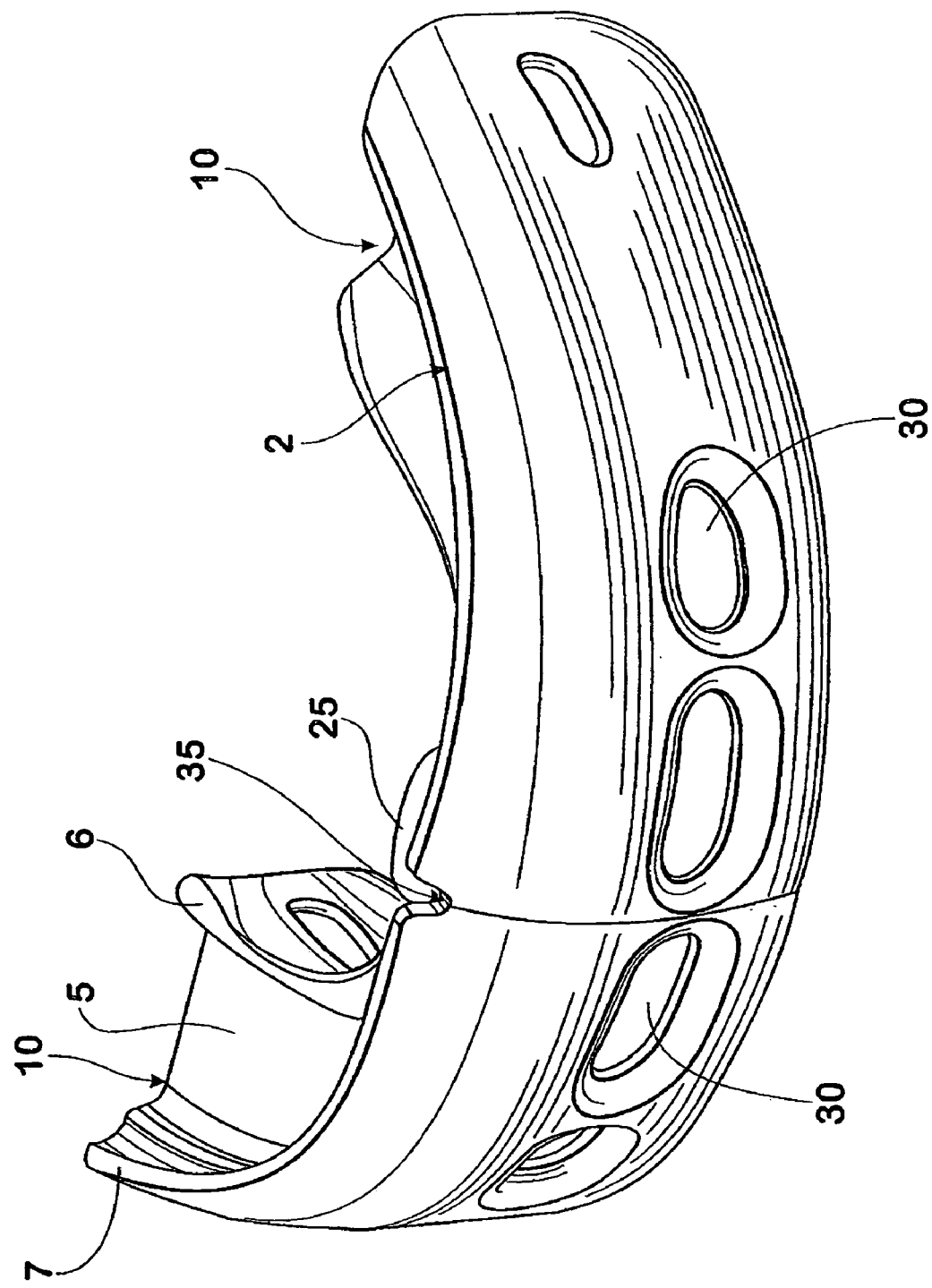
FIG. 4 is a front three dimensional view of the base member of the appliance of FIG. 1.
Figure 5:
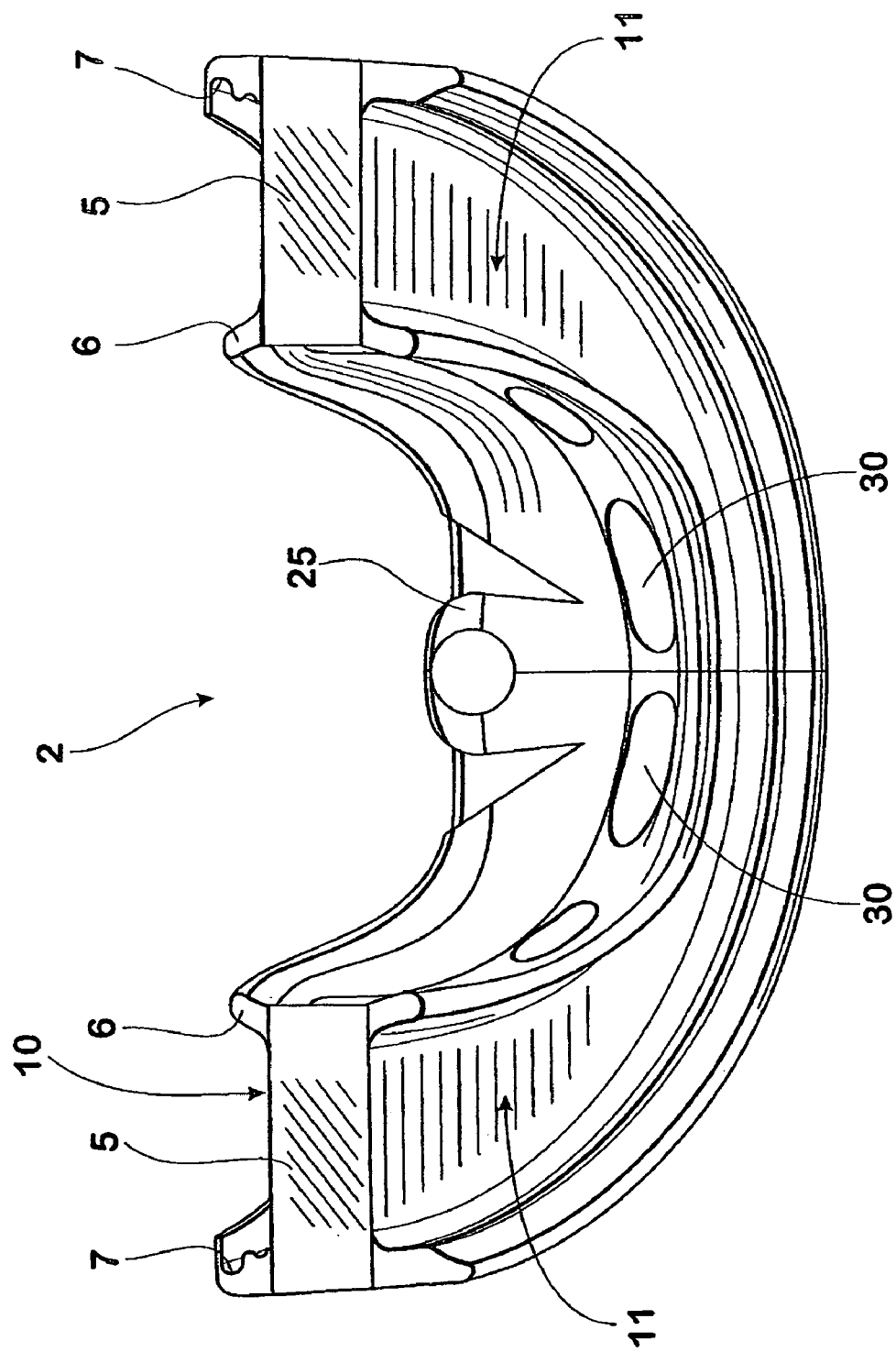
FIG. 5 is a rear three dimensional view of the base member of FIG. 4.

In FIGS. 1 to 5 reference numeral 1 refers generally to an appliance in accordance with the invention.

The appliance 1 comprises broadly a base member 2 and two teeth engaging elements 3 and 4.

The base member 2 has a broadly U-shaped configuration sized to complement the general U-shape of the jaw of a user when viewed in plan view. The base member 2 has a central web 5 and inner and outer flanges 6 and 7 projecting both upwardly and downwardly from both the inner and outer edges of the web 5.

The web 5 and flanges 6 and 7 collectively define upper and lower channels 10 and 11 within which respectively the upper and lower teeth engaging elements 3 and 4 are positioned.

The base member 2 is made of a substantially rigid plastic material having an appropriate mechanical strength. Polypropylyne, polyurethane and santoprine have been found to be very suitable although other plastics may also be used. Polyurethane has been used in the illustrated embodiment.

Each of the elements 3, 4 is made of a thermoplastic material which in the illustrated embodiments is EVA. The EVA softens at 90 to 95° C. and thus can be softened by placing in boiling water.

Each of the tooth engaging elements 3 and 4 also has a broadly U-shaped configuration when viewed in plan view. This complements the general shape of the base member 2. Each element 3, 4 also has a broadly U-shaped cross sectional configuration with a bottom wall 15 and two side walls 16 and 17. The shape and width of the channels defined in the base member 2 and elements 3 and 4 have been specifically designed so as to enable the appliance to accommodate widely varying jaw widths and thereby be capable of being fitted to a large number of patients. The appliance also includes a notch or cut-out 35 in the upper surface of the outer flange 7. The notch 35 has the important function of permitting inward or outward adjustment of the arms of the U-shaped member without causing distortion of the appliance 10. This assists in fitting a single size appliance to patients with widely different arch sizes.

In the illustrated embodiment, the layer of EVA forming the elements 3, 4 extends continuously across the full surface area of the base member including the outer surface of the flanges 6 and 7 and thus covers more than just the U-shaped channels of the base member 2. The reason for applying the layer of thermoplastic material across the entire surface area of the base member is to mount or attach the EVA layer to the base member which is made of polyurethane, polypropylene or santoprine. EVA does not bond naturally to the base member when it is moulded onto the base member and thus a way has to be found of securing it to the base member. This is accomplished by mechanically encasing or enclosing the base member within the layer of EVA. The inability of EVA to bond to the plastic base member is a major problem to be overcome in manufacturing these appliances.

The appliance has a tongue tag 25 for positioning the tongue in an exact central position. The appliance also has a plurality of holes 30 defined therein that permit mouth breathing. This is essential for playing sports.

A further feature of the appliance is that the web of the base member 2 tapers outwardly from the leading edge thereof up to a point thickening the web, and then tapers inwardly after that to the rear end progressively thinning the web. Thus, the web has a cross sectional configuration so as to substantially occupy the space between the teeth of upper and lower jaws of the user. This configuration which is clearly illustrated in the applicant's prior applications may generally be described as an asymmetrical aerofoil shape having a curved surface on the lower side. The web may have a thickness of about 6 mm at its thickest point.

This supports the jaw of a user and encourages the lower jaw to assume its anatomically correct position relative to the upper jaw. This is believed to cause a relaxation of muscles in the head and the neck. This configuration of the web of the base member opens the "bite" and holds the jaw in a more down and forward position. In this position, the jaw is more resistant to injury. This jaw position is understood to enhance athlete performance. Further, the thickening of the web naturally also strengthens the appliance.

The appliance 1 is made in a two-step injection moulding process. The base member 2 is injection moulded in a first die from polyurethane. The base member 2 is then switched to a second die having a larger cavity and the layer of EVA, including the teeth engaging members 3, 4, is then moulded onto the base member.

The injection moulding process comprises broadly the injection of a viscous resin from a heated cylinder into the die by means of a plunger or injector. The die is cooled by cooling means, e.g. chilled cooling water, causing the resin to cure and harden. The moulded article can then be removed from the die. The injection moulding techniques used to form the appliance would be well known to a person skilled in the art and do not form part of the invention. Therefore, they will not be described in further detail.

In use, the mouth guard may be in one example application be fitted by a dentist in a dental surgery. In other applications, the guard may be fitted by a user. This is done by heating the appliance up to 90° C. by soaking it in boiling water. When this occurs the base member remains rigid while the elements 3, 4 soften making them suitable for being customised to the individual tooth and jaw shape of a user. The appliance is then placed in position in the mouth of a user and the elements 3, 4 conform to the user's teeth and jaw and then harden in this position.

Figure 6:
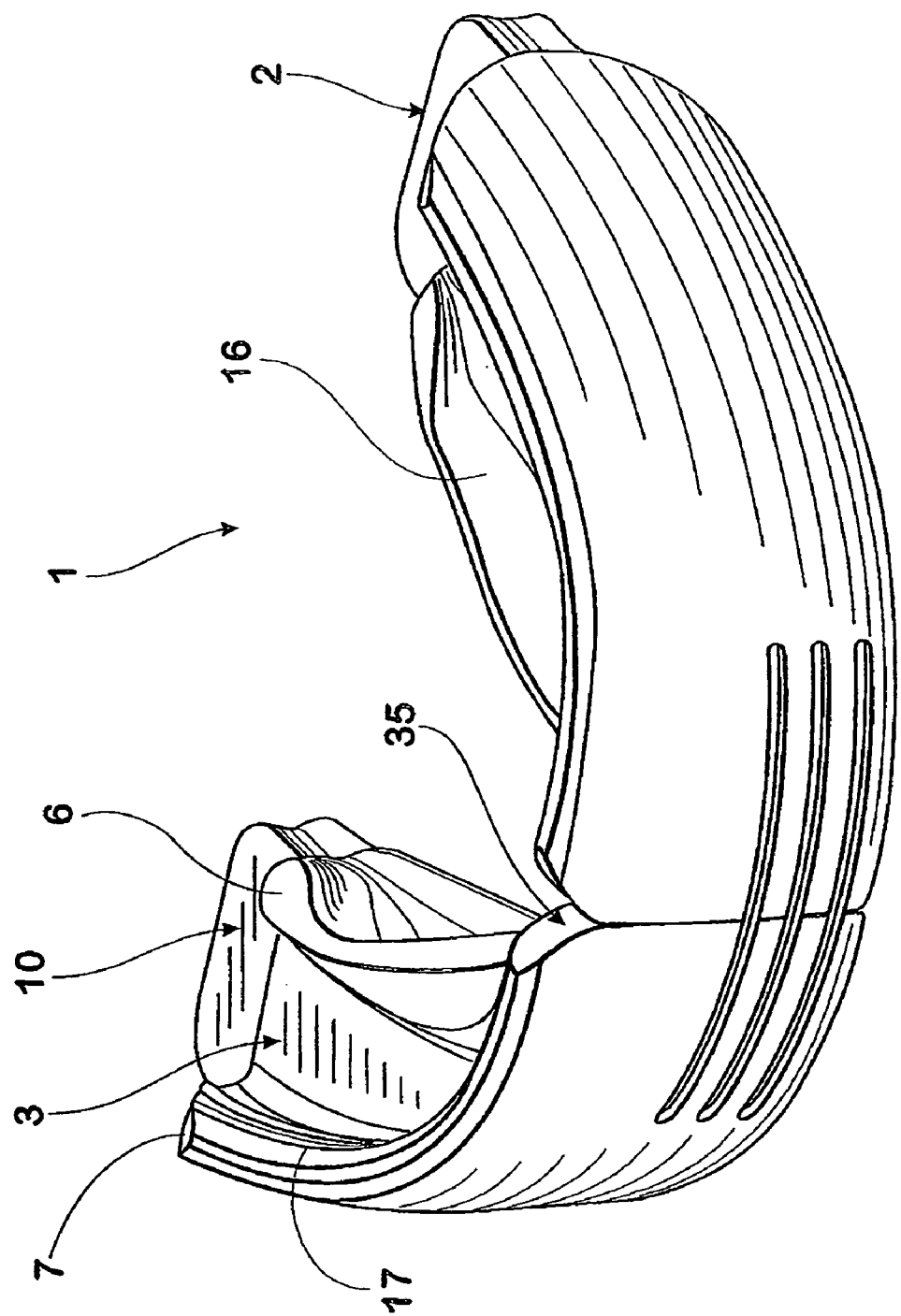
FIG. 6 is a front three dimensional view of an appliance in accordance with a second embodiment of the invention.
Figure 7:
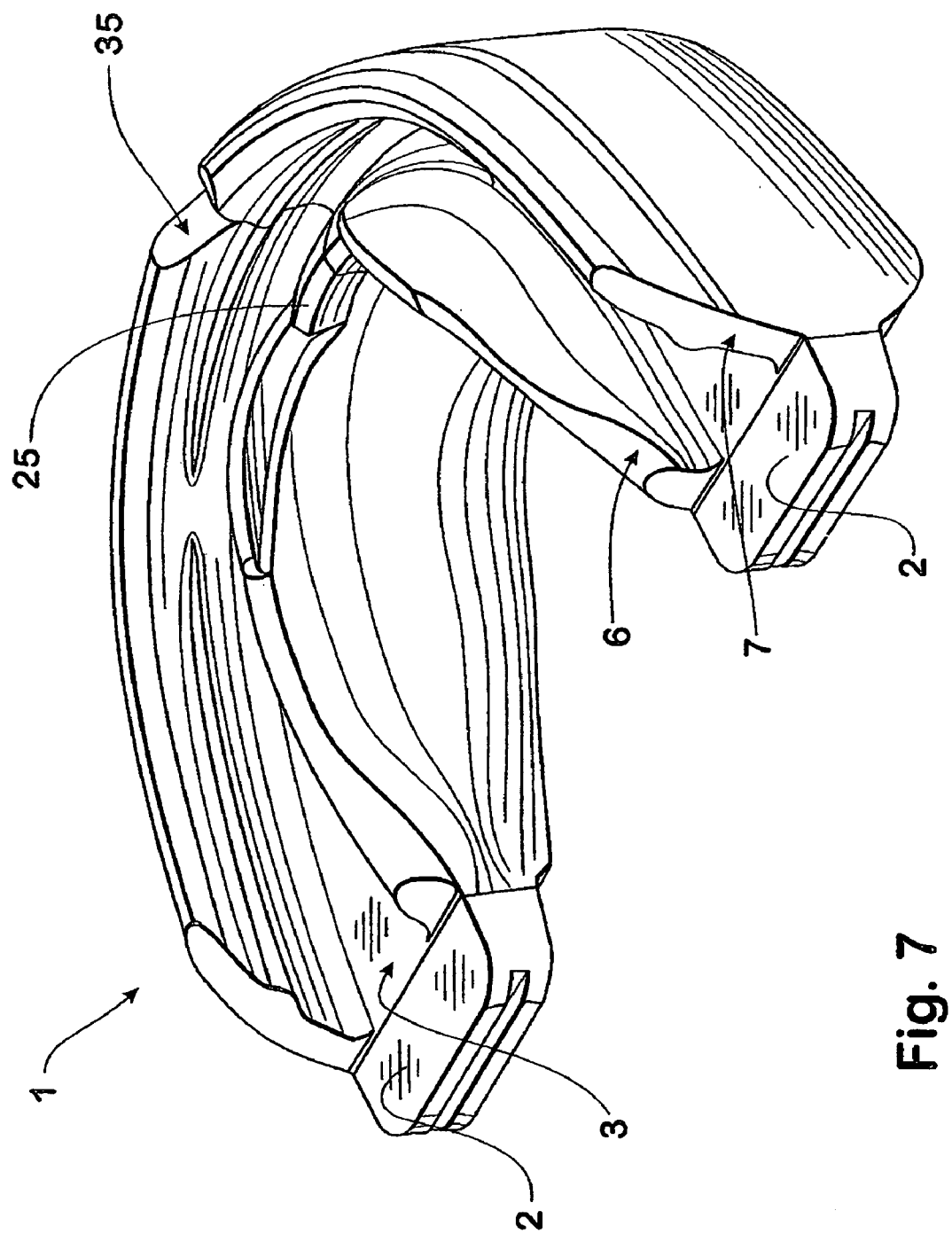
FIG. 7 is a rear three dimensional view of the appliance of FIG. 6.
Figure 8:
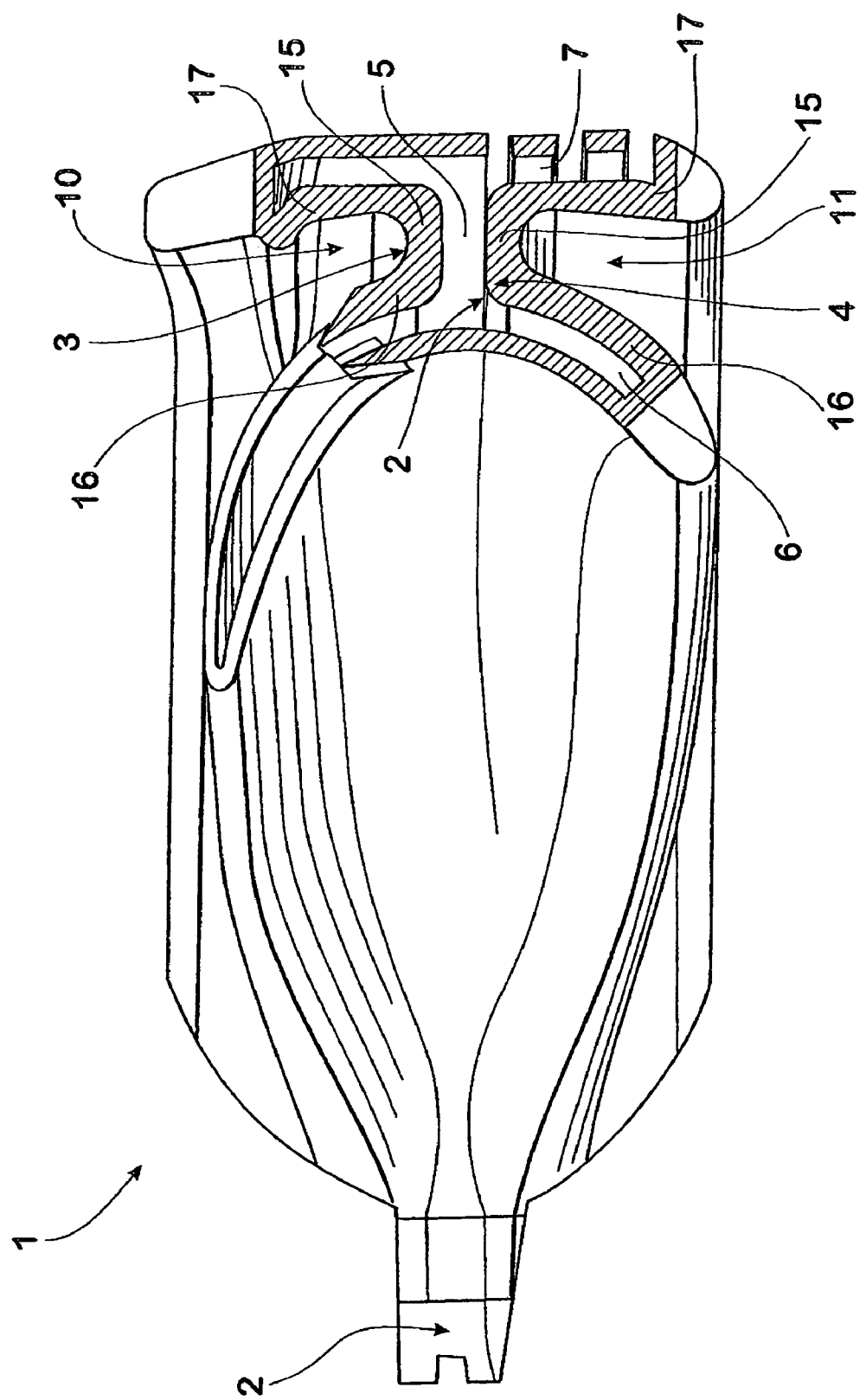
FIG. 8 is a part sectional side view of the appliance of FIG. 6.
Figure 9:
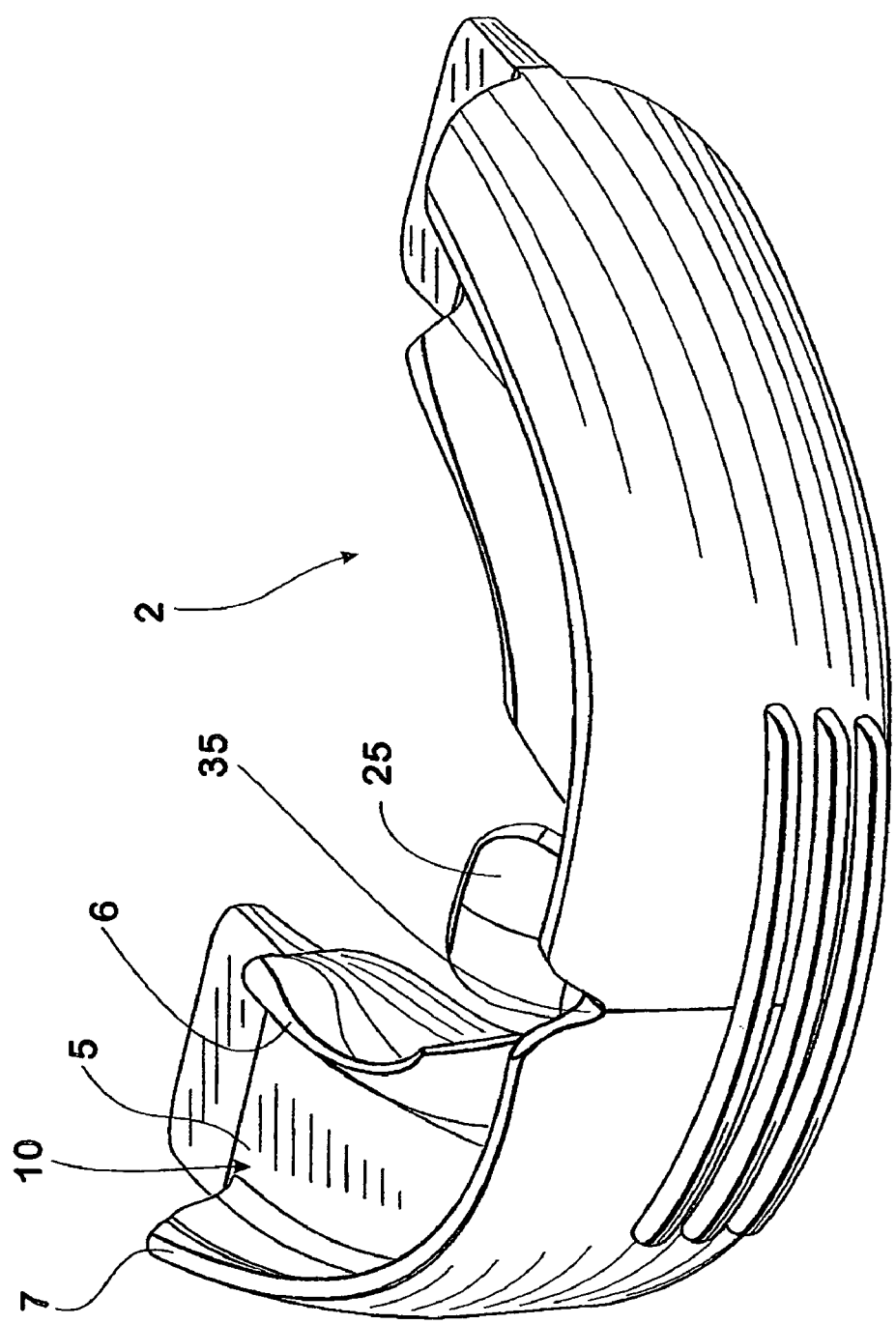
FIG. 9 is a front three dimensional view of the base member of the appliance of FIG. 6.
Figure 10:
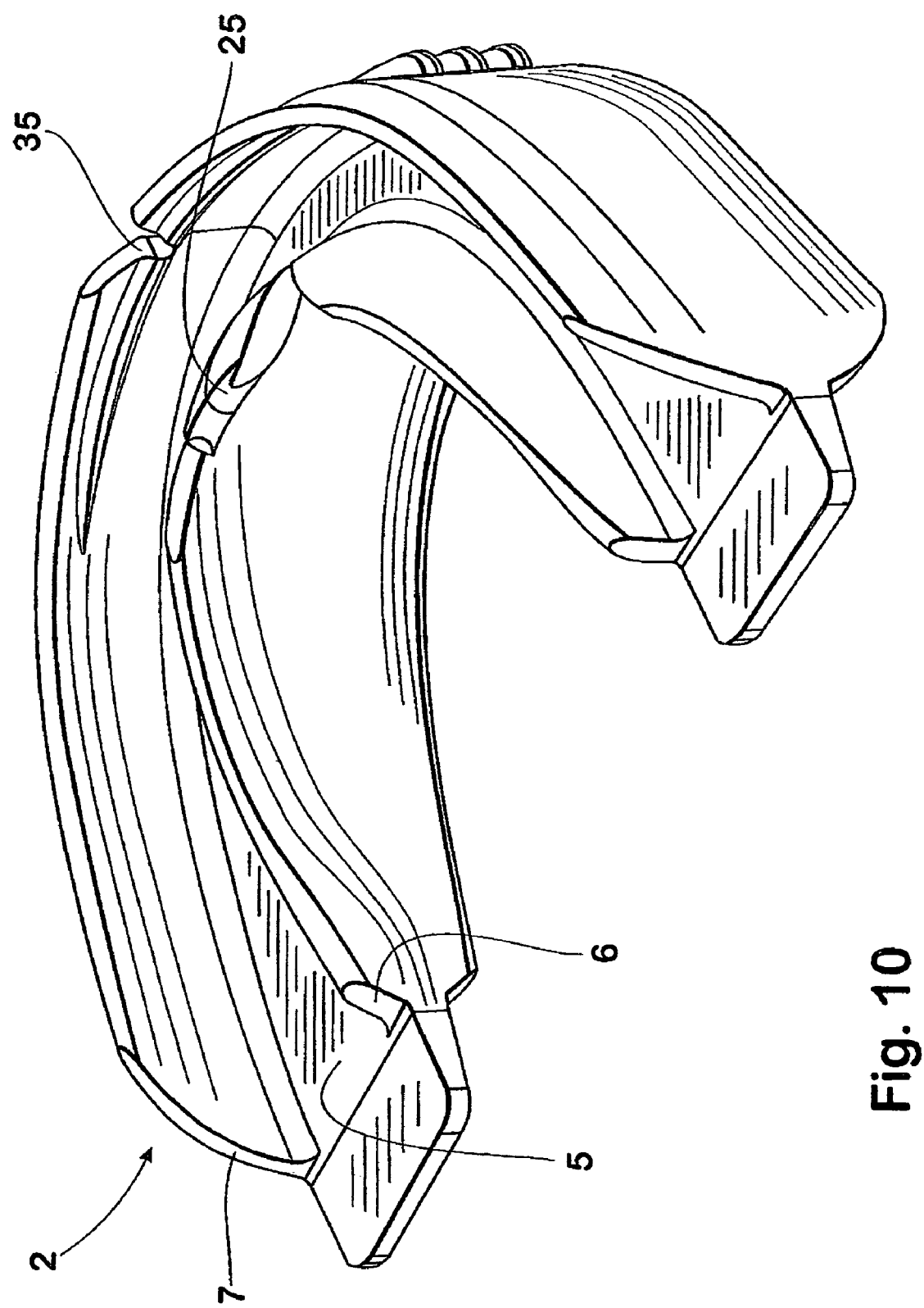
FIG. 10 is a rear three dimensional view of the base member of FIG. 9.
Figure 11:
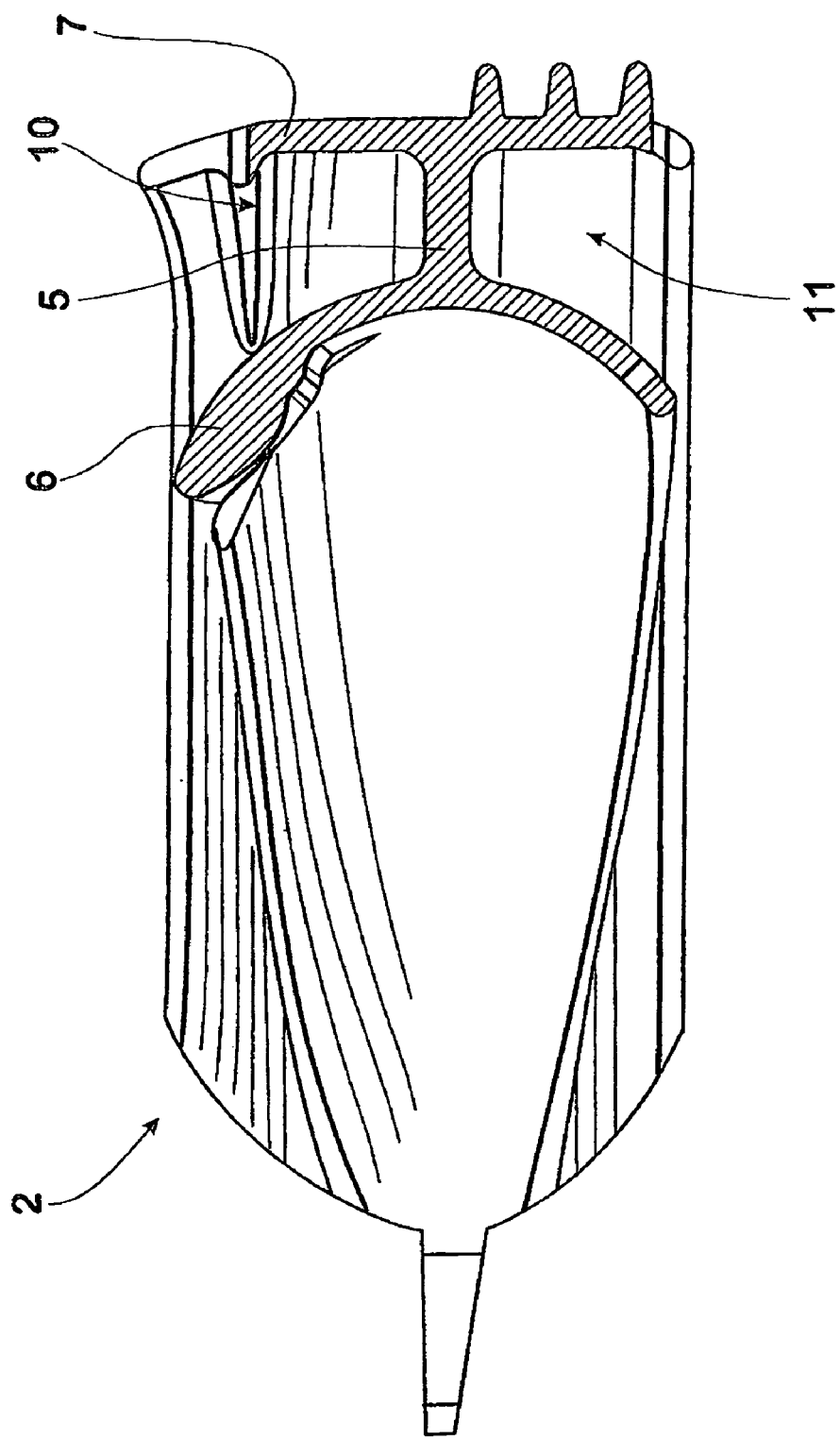
FIG. 11 is a sectional side view of the base member of FIG. 9.

In a second embodiment of the invention illustrated in FIGS. 5 to 11, the appliance is used for orthodontic treatment. The orthodontic appliance is the same as that illustrated in FIGS. 1 to 5 with the exception that it does not have breathing holes, e.g. for mouth breathing, and the base element 2 is thinner, e.g. having an approximate thickness of 2 mm to 4 mm, because it does not have the same requirements of mechanical strength as the sports guard. The orthodontic appliance is used for myofunctional training and tooth realignment.

Myofunctional training is a clinical procedure which is designed to correct bad oral habits, e.g. tongue thrusting, mouth breathing, incorrect swallowing and the like.

In use the appliance is initially fitted by a dentist or orthodontist in a dental surgery. The shape of the elements 3, 4 prior to use corresponds broadly to an ideal positioning or "bite" of a patients teeth. To enable the elements 3, 4 to be tailored to a patients specific teeth, the elements 3, 4 are dipped into boiling water to soften the elements and then inserted into a patients mouth to mould them to the specific contours of a patient's mouth.

The EVA material from which the elements 3, 4 are formed has a memory so that it reverts to its original shape when reheated. It reverts partly to its original shape when heated to 60 to 65° C. and fully to its original shape when heated above 90° C.

The memory properties of the EVA enable the elements 3, 4 to be used to progressively correct misalignment of a patients teeth. For example at spaced time intervals, the dentist will typically place the appliance into water at a temperature of 60–65° C. which causes the elements 3, 4 to partly revert to their original shape. The slightly altered shape brought about by this remoulding causes the appliance to apply pressure to the teeth of a user to correct misalignment. This can be done several times until the patients teeth take up the correct position or the ideal "bite" position.

When the teeth are in the correct position the appliance can be placed into water at 90–95° C. which causes it to revert fully to its original position. The appliance can then be used as a retaining device for retaining the teeth in the correct position and also for carrying out myofunctional training.

An advantage of the appliance described above is that it enables industrially manufactured mouth guards to be customised to a user's mouth very easily and simply, e.g. in a dentist's chair or by a user. A further advantage is that the appliance can be applied equally to orthodontic and sports guard applications. A yet further advantage of the appliance is that it effectively attaches the EVA elements to the base member.

The sports mouth guard described above is very effective because it protects both upper and lower teeth and also the jaw joints. The orthodontic appliance provides an inexpensive device for correcting myofunctional and tooth alignment problems.

It will of course be realised that the above has been given only by way of illustrative example of the invention and that all such modifications and variations thereto as would be apparent to persons skilled in the art are deemed to fall within the broad scope and ambit of the invention as is herein set forth.

What is claimed is:

1. An oral appliance for placing in a mouth of a user, the appliance including:
   a base member having a generally U-shaped form corresponding to the outline of a jaw of a user, the base member having inner and outer flanges interconnected by a web which define at least one of upper and lower channels within which the corresponding rows of teeth of a user are received, said base member being made of a plastics material which is rigid and non-thermoplastic at a temperature of 90° C.–95° C.; and
   a continuous layer of thermoplastic material that encompasses the base member thereby to firmly and securely mount the layer of thermoplastic material on the base member, the layer of thermoplastic material forming teeth engaging elements which can be conformed or moulded to suit the individual teeth of a user by heating to a temperature at which the layer is plastic and formable.

2. An oral appliance according to claim 1, wherein the base member defines an upper channel within which the upper row of teeth of a user is received.

3. An oral appliance according to claim 1, wherein the base member defines both upper and lower channels within which respectively the upper and lower rows of teeth of a user are received.

4. An oral appliance according to claim 1, wherein the layer of thermoplastic material is EVA (ethylvinylacetate) which is plastic at a temperature of 90° C.–95° C. and the base is made out of a polymer from the group consisting of polyurethane, polypropylene and santoprine.

5. An oral appliance according to claim 1, wherein the layer of thermoplastic material forming the teeth engaging elements has a thickness of 1 mm–3 mm and wherein said continuous layer of thermoplastics material substantially covers the full surface area of the base member.

6. An oral appliance according to claim 1, wherein a tongue tag is formed on the inner flange of the base member, the tongue tag being substantially centrally positioned for correctly positioning the tongue of a user during use and the base member has breathing apertures defined therein for facilitating breathing by a user when wearing the appliance, and a notch defined in an upper surface of the outer flange for permitting inward or outward adjustment of the U-shaped member.

7. A method of manufacturing an oral appliance for placing in the mouth of a user, the method including the steps of:

moulding a base member from plastic material in a first moulding step in a first mould, the member having a generally U-shaped form corresponding to the outline of the jaw of a user and inner and outer flanges interconnected by a web which define at least one of upper and lower channels within which the corresponding rows of teeth of a user are received, the base member being made of plastics material which is rigid and non-thermoplastic at a temperature of 90°–95° C.;

removing the base member from the first mould and placing it in a second mould having a larger mould cavity and moulding a continuous layer of thermoplastic material onto the base member to form upper and lower teeth engaging elements capable of being customized to suit the mouth of a user, the layer encasing the member to thereby firmly and securely mount the layer of thermoplastic material on the base member.

8. A method according to claim 7, wherein the base member defines an upper channel within which the upper row of teeth of a user is received or the base member defines both upper and lower channels within which respectively the upper and lower rows of the teeth of a user are received.

9. A method according to claim 7, wherein the continuous layer of thermoplastic material is moulded substantially fully across the surface area of the base member in said second moulding step and wherein the layer of thermoplastic material is injection moulded from EVA while it is locked in position in the second mould.

10. A method according to claim 7, wherein the base member is injection moulded from a polymer from the group consisting of polyurethane, polypropylene or santoprine.

* * * * *